(12) United States Patent
Klein (10) Patent No.: US 9,476,843 B2
(45) Date of Patent: Oct. 25, 2016

(54) DEVICE FOR MEASURING THE DIELECTRIC AND/OR MAGNETIC PROPERTIES OF A SAMPLE BY MEANS OF A MICROWAVE TRANSMISSION MEASUREMENT

(71) Applicant: Elisabeth Katz, Simmersfeld (DE)

(72) Inventor: Albert Klein, Simmersfeld (DE)

(73) Assignee: Elisabeth Katz, Simmersfeld (DE)

( * ) Notice: Subject to any disclaimer, the term of this patent is extended or adjusted under 35 U.S.C. 154(b) by 0 days.

(21) Appl. No.: 14/402,311

(22) PCT Filed: May 16, 2013

(86) PCT No.: PCT/EP2013/001446
§ 371 (c)(1),
(2) Date: Nov. 19, 2014

(87) PCT Pub. No.: WO2013/174493
PCT Pub. Date: Nov. 28, 2013

(65) Prior Publication Data
US 2015/0091585 A1 Apr. 2, 2015

(30) Foreign Application Priority Data
May 25, 2012 (DE) .......... 10 2012 010 255

(51) Int. Cl.
*G01N 22/00* (2006.01)
*G01N 22/04* (2006.01)
*G01N 22/02* (2006.01)

(52) U.S. Cl.
CPC .............. *G01N 22/00* (2013.01); *G01N 22/04* (2013.01); *G01N 22/02* (2013.01)

(58) Field of Classification Search
CPC ....... G01N 22/00; G01N 22/02; G01N 22/04
USPC ................. 324/639, 637, 629, 600
See application file for complete search history.

(56) References Cited

U.S. PATENT DOCUMENTS 5,112,190 A 5/1992 Kajiwara et al.
6,163,158 A 12/2000 Moeller et al.
(Continued)

FOREIGN PATENT DOCUMENTS

| DE | 3915280 C2 | 11/1993 |
| DE | 19734978 A1 | 2/1999 |
| DE | 102010041572 B3 | 3/2012 |
| EP | 0 990 887 A2 | 4/2000 |

OTHER PUBLICATIONS

Wu T Y et al, "The acurate measurement of microwave phase-shift using a dual-channel heterodyne system", Microwave Conference, 2009. APMC 2009. Asia Pacific, IEEE, Dec. 7, 2009, pp. 1597-1600.
(Continued)

*Primary Examiner* — Hoai-an D Nguyen
(74) *Attorney, Agent, or Firm* — Rabin & Berdo, P.C.

(57) ABSTRACT

A device for measuring at least one of dielectric and magnetic properties of a sample by means of a microwave transmission measurement includes a transmitting antenna and a receiving antenna defining a transmission measuring section in which the sample to be measured is located, and transmitting and receiving modules. The transmitting and receiving modules include one or more transmission-side and receiving side synthesizers, a clock, one or more transmission side or receiving side mixers to generate intermediate-frequency signals based on high-frequency signals received from the synthesizers, and at least one evaluation unit to perform an evaluation based on the intermediate-frequency signals.

6 Claims, 7 Drawing Sheets

(56) References Cited

U.S. PATENT DOCUMENTS

| | | | |
|---|---|---|---|
| 6,249,129 B1* | 6/2001 | Burk | C13B 25/06 324/639 |
| 7,908,930 B2* | 3/2011 | Xie | G01N 22/00 73/861.04 |
| 2011/0267074 A1 | 11/2011 | Xie et al. | |
| 2012/0074957 A1 | 3/2012 | Schroeder | |

OTHER PUBLICATIONS

Seichi Okamura et al, "A new microstripline-type moisture sensor for heavily wet tea leaves", Measurement Science and Technology, KR, vol. 18, No. 4, Apr. 1, 2007, pp. 1022-1028.

Office Action issued by German Patent and Trademark Office for corresponding German application DE 10 2012 010 255.0.

* cited by examiner

DEVICE FOR MEASURING THE DIELECTRIC AND/OR MAGNETIC PROPERTIES OF A SAMPLE BY MEANS OF A MICROWAVE TRANSMISSION MEASUREMENT

TECHNICAL FIELD OF THE INVENTION

The invention relates to a device for measuring the dielectric and/or magnetic properties of a sample by means of a microwave transmission measurement, as defined in the preamble to claim 1.

PRIOR ART

Known from the prior art are numerous options for the contactless measuring of the dielectric properties of a sample, for example the moisture. For example, it is possible to transmit a microwave through the sample and to obtain the desired information by comparing the irradiated microwave, or a signal derived from it, to the transmitted microwave, or to a signal derived from it. The absorption as well as the phase shift can be determined in the process, so that the complete information on the complex epsilon of the sample can be obtained from the respective measurement. A suitable device comprises a transmitting module and a receiving module. The transmitting module is provided with at least one synthesis generator (also referred to as synthesizer) for generating a high-frequency signal and a transmitting antenna that is connected to the synthesizer. The synthesizer is clocked by a so-called frequency standard which emits a low-frequency signal, for example with a frequency of 10 MHz The high-frequency signal generated by the at least one synthesizer is furthermore transmitted to the receiving module, which is also provided with a receiving antenna, and is mixed therein with the microwave received at the receiving antenna. Also provided is an evaluation unit which can be embodied as separate module. The mixed signal is transmitted to this evaluation unit.

A distinction is basically made between two types of measuring systems, namely so-called homodyne systems that operate with only a single frequency and have only one synthesizer, and so-called heterodyne systems which operate with two closely adjacent frequencies and two synthesizers. Both systems have in common that they operate by comparing two microwaves, wherein one microwave passes through the sample and thus experiences attenuation and/or a phase shift, while the other microwave does not pass through the sample and functions as a reference. A high-frequency reference line must therefore be provided between the transmitting module and the receiving module (this applies to homodyne as well as heterodyne systems). Under laboratory conditions, providing such a high-frequency line is generally not a problem since no long local distances must be overcome on the one hand and, on the other hand, constant conditions prevail in the laboratory, especially substantially constant temperatures.

However, if a device of this type is used for industrial purposes, providing such a high-frequency reference line carries some problems and disadvantages, in particular since the temperature dependence on the wave propagation speed in a coaxial cable has an increasingly higher effect on the phase shift, the higher the frequency. It means that with non-constant environmental conditions, especially temperatures, considerable phase shifts can occur in the high-frequency reference line and the antenna feed lines which distort the measuring result. When used on an industrial scale, the transmitting module and the receiving module can furthermore be spaced very far apart, which makes this problem worse, especially in cases where such an arrangement is installed totally or partially in the open, so that it can be subject to irradiation from the sun.

OBJECT OF THE INVENTION

Starting therefrom, it is the object of the present invention to improve a generic device in such a way that it is better suited for the use in industrial applications, in particular, and delivers constant and good measuring results even with fluctuating environmental conditions.

This object is solved with a device having the features as disclosed in claim 1.

The core idea behind the invention must be seen in providing at least one synthesizer for generating a high-frequency signal on the transmitting side as well as the receiving side and in coupling these two synthesizers in a phase-locked reproducible manner, for which a joint frequency standard is provided which actuates the two synthesizers via respectively at least one low-frequency signal line, which is referred to as low-frequency synchronization signal line. The use of the aforementioned, problematic high-frequency reference line is thus rendered unnecessary when providing a synthesizer on the receiving side, according to the invention. Low-frequency signal lines of this type are nearly insensitive to the aforementioned environmental influences, even at long lengths, so that no re-calibration is required even for strongly fluctuating environmental influences, in particular considerable changes in the temperature. A device of this type according to the invention can in principle be embodied as a homodyne system as well as a heterodyne system, wherein the embodiment as a heterodyne system is generally preferred.

Preferred embodiments of the invention follow from the dependent claims as well as from the exemplary embodiments which are explained in further detail in the following with reference to the Figures, which show in:

Figure 3:
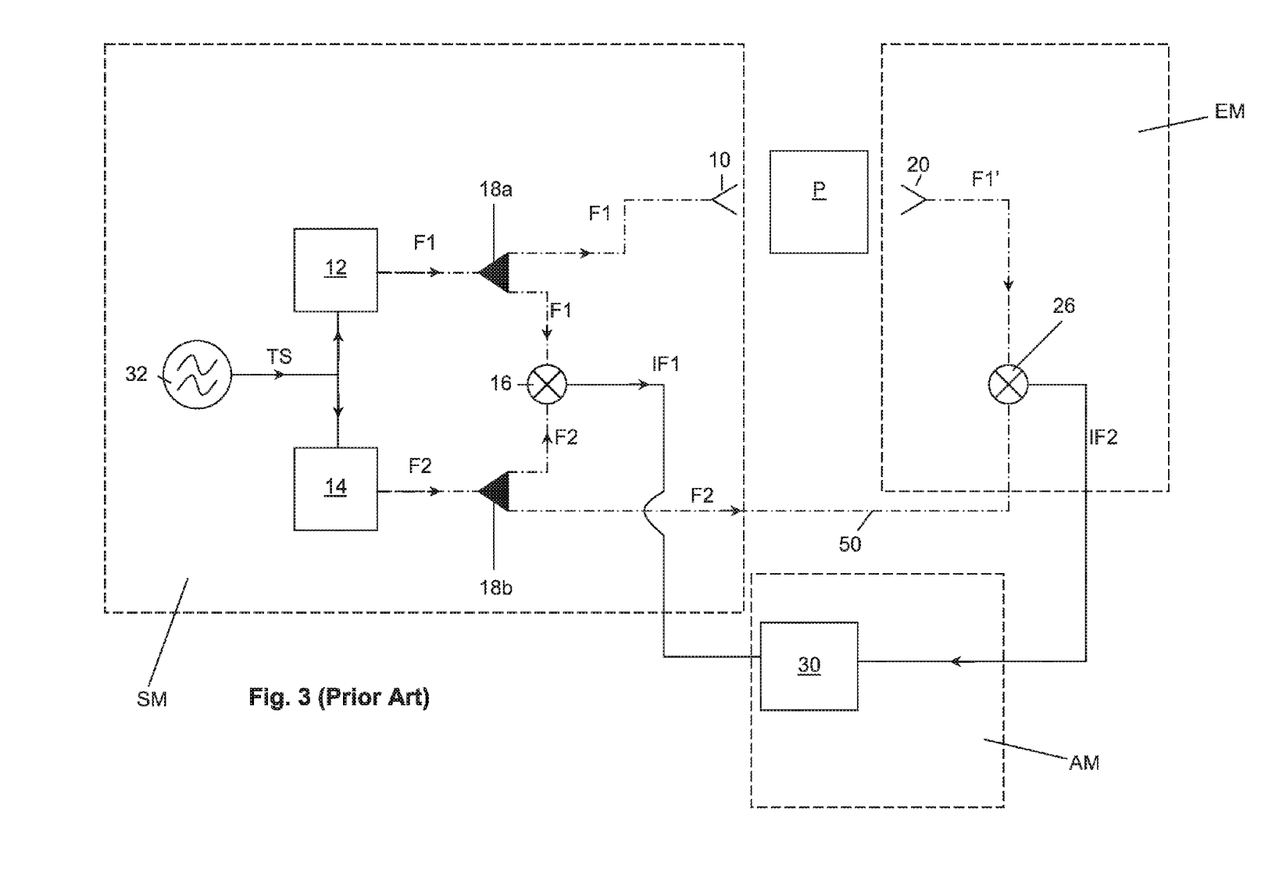
FIG. 3 A circuit diagram for a heterodyne system according to the prior art.

For a better understanding of the invention, we first want to discuss the prior art upon which the present invention is based in further detail and with reference to FIG. 3.

As previously mentioned, FIG. 3 shows a device for measuring the dielectric and/or magnetic properties of a sample P, wherein the device is embodied as a heterodyne measuring system. This system can be viewed as consisting of three modules, namely a transmitting module SM, a receiving module EM, and an evaluation unit. Usually, the transmitting module SM and the receiving module EM are spatially separated. The evaluation unit can be embodied as a physically separate evaluation module AM, but can also be integrated into one of the other two modules, for example the transmitting module SM. Functionally, however, these three elements can always be viewed as separate modules. A transmitting antenna 10 and a receiving antenna 20 define a transmission measuring section into which a sample P can be placed. In this application, "antenna" is understood to refer to each element which is suitable for transmitting and/or receiving a freely propagating microwave or a microwave conducted inside a waveguide, wherein the antenna can also be embodied integrally with another component.

The following definitions and conventions apply for the text below:

electromagnetic waves which propagate inside a conductor or which propagate freely and have a frequency between 800 MHz and 30 GHz are referred to as "high-frequency signal" or "microwave." High-frequency signal lines (microwave conductors) suitable for these types of frequencies are known from the prior art. The high-frequency signal lines are shown as dash-dot lines in the Figures (this is true for the prior art FIG. 3, as well as for FIGS. 1 and 2). The term "low-frequency" is understood to refer to all electromagnetic waves or signals having a frequency below 200 MHz Signal lines used for the transmission of such low-frequency signals are here referred to as low-frequency signal lines and are shown in the drawings as solid lines. For reasons of clarity, not all signal lines (be it high-frequency signal lines or low-frequency signal lines) are given a separate name/reference symbol in the description and the drawings. The high-frequency signal lines as well as the low-frequency signal lines are generally physically embodied as coaxial cables, wherein for reasons of cost, coaxial cables of a higher quality are generally used for the high-frequency signal lines than for the low-frequency signal lines. However, this is not absolutely required, and sufficiently high-quality coaxial cables could be used for all signal lines. Insofar, the terms "high-frequency signal line" and "low-frequency signal line" should above all be understood to be functional terms.

In addition to the transmitting antenna 10, the transmitting module SM comprises two transmitting-side synthesizers 12 and 14, two power dividers 18a, 18b, one transmitting-side mixer 16 and and a frequency standard 32. The receiving module EM comprises only a receiving-side mixer 26 in addition to the receiving antenna 20. The evaluation module AM is composed of a central processor 30 as the evaluation unit. The transmitting module SM and the receiving module EM are connected via a high-frequency reference line 50. The transmitting module SM and the receiving module EM are respectively connected to the evaluation module AM (meaning to the central processor 30) via a separate low-frequency signal line (lF1; lF2). The mode of operation is as follows:

The frequency standard 32 clocks the two transmitting-side synthesizers 12, 14, wherein the clocking frequency, for example, can be 10 MHz The first transmitting-side synthesizer 12 generates a first high-frequency signal F1 with a first high frequency of 3 GHz, for example, and the second transmitting-side synthesizer 14 generates a second high-frequency signal F2 with a slightly different high frequency, for example 3.001 GHz. The first high-frequency signal F1 of the first transmitting-side synthesizer 12 is supplied to a power divider 18a, the first output of which is connected to the transmitting antenna 10 while its second output is connected to the transmitting-side mixer 16. The second transmitting-side synthesizer 14 is connected to the second power divider 18b, the outputs of which are connected to the transmitting-side mixer 16 and via the high-frequency reference line 50 to the receiving-side mixer 26. The second input of the receiving-side mixer 22 is connected to the receiving antenna 20.

The transmitting-side mixer 16 thus generates a first intermediate-frequency signal lF1 with a first intermediate frequency which represents the difference between the first high frequency (also the frequency of the transmitted microwave) and the second high frequency, meaning it amounts to 1 MHz for the selected example. The receiving-side mixer 26, in turn, generates a second intermediate-frequency signal lF2 that represents the difference between the received microwave (this signal is given the reference F1') and the second high frequency signal from the second transmitting-side synthesizer 14. In this case, F1 and F1' have identical frequencies since the transmission through the sample P changes the phase and the amplitude, but not the frequency. For that reason, the two intermediate frequency signals lF1 and lF2 also have the same intermediate frequency, in this case 1 MHz. From the comparison between the first intermediate-frequency signal lF1 and the second intermediate frequency signal lF2, it is possible to deduce, in a manner known per se, the phase shift as well as the attenuation experienced by the microwave emitted by the transmitting antenna 10 when it passes through the sample P. In turn, it is possible to deduce from this the dielectric properties of the sample. The corresponding calculations are carried out by the evaluation module AM, namely by the central processor 30.

DESCRIPTION OF THE PREFERRED EMBODIMENTS

Figure 1:
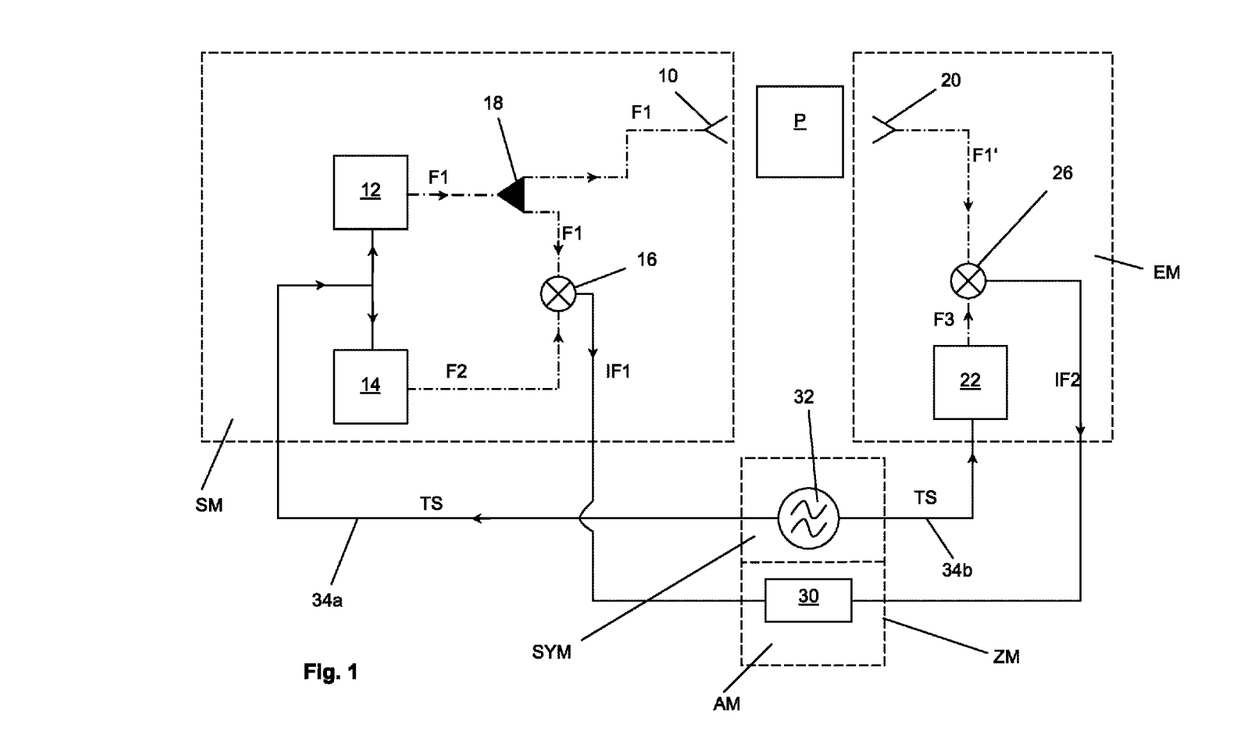
FIG. 1 The circuit diagram for a first exemplary embodiment of the invention.

With reference to FIG. 1, a device according to the invention is now described, which is also embodied as a heterodyne system, as the above-described device according to the prior art. In the same way as the aforementioned device, the device according to the invention can be seen as being composed of three modules, namely a transmitting module SM, a receiving module EM, and a central module ZM which comprises the evaluation module AM—meaning the evaluation unit—as well as a synchronization module SYM which does not exist in this form in the prior art. The three modules here also do not absolutely have to be embodied as locally separated modules, but for the sake of clarity we will retain the above-used terminology. However, it should be taken into consideration that in particular the transmitting module SM and the receiving module EM are in practice frequently embodied as physically separate modules. The central module ZM can be integrated into one of the modules.

In the same way as for the prior art, the transmitting module SM comprises two transmitting-side synthesizers 12 and 14 which respectively generate a high-frequency signal F1 and F2, wherein these high frequencies differ slightly, for example the first high frequency can be 3 GHz and the second high frequency can be 3.001 GHz. As described above with reference to the prior art, the first transmitting-side synthesizer 12 also feeds its high-frequency signal F1 into a power divider 18 which, in turn, is connected to a transmitting-side mixer 16 and the transmitting antenna 10. The second transmitting-side synthesizer 14 feeds the second high-frequency signal F2, generated by it, directly into the transmitting-side mixer 16 which, in the same way as for the prior art, is connected to the evaluation module AM, namely to the central processor 30.

In contrast to the prior art, the transmitting module SM is not connected via a high-frequency reference line to the receiving module EM which is the reason why no second power divider is provided. Instead, the receiving module EM comprises a receiving-side synthesizer 22 which generates the same high frequency as the second transmitting-side synthesizer 14 which, for the selected example, is 3.001 GHz. This receiving-side synthesizer 22 feeds the third high frequency-signal F3, generated by it, into the receiving-side mixer 26, wherein the second input of this mixer is connected to the receiving antenna 20, so that it receives the first high-frequency signal F1' transmitted through the sample.

As for the prior art, the transmitting side mixer 16 generates a first intermediate frequency signal IF1 and the receiving-side mixer 26 also generates a second intermediate-frequency signal IF2, wherein the two intermediate frequencies are the same, namely 1 MHz for the herein described example. These two intermediate-frequency signals IF1 and IF2 are supplied, in the same was as for the prior art, to the evaluation module AM, meaning they are fed to the central processor 30. In order to deduce from the phase shift between the first intermediate frequency signal IF1 and the second intermediate-frequency signal IF2 a relevant conclusion on the phase shift experienced by the first high-frequency signal F1 when passing through the sample P, all synthesizers 12, 14 and 22 must be synchronized. The synchronization is ensured by the synchronization module SYM, meaning by the frequency standard 32, which is connected via a transmitting-side low-frequency synchronization signal line 34a to the two transmitting-side synthesizers 12, 14 and via a receiving side low-frequency synchronization signal line 34b to the receiving side synthesizer 22 and which emits a clocking signal TS by means of which the synthesizers are coupled phase-locked reproducible. The "heart" of such a frequency standard is generally a quartz oscillator, the resonance frequency of which is used as normal frequency. Typically, this normal frequency ranges from 1 to 30 Mhz, in particular 10 MHz, as selected for this example. Both low-frequency synchronization signal lines 34a, 34b are low-frequency signal lines that are preferably embodied physically identical, in particular having the same length and identical design. As a result, the use of a high-frequency reference line that connects the transmitting module SM and the receiving module EM can be omitted, thereby resulting in the improvement according to the invention.

Figure 2:
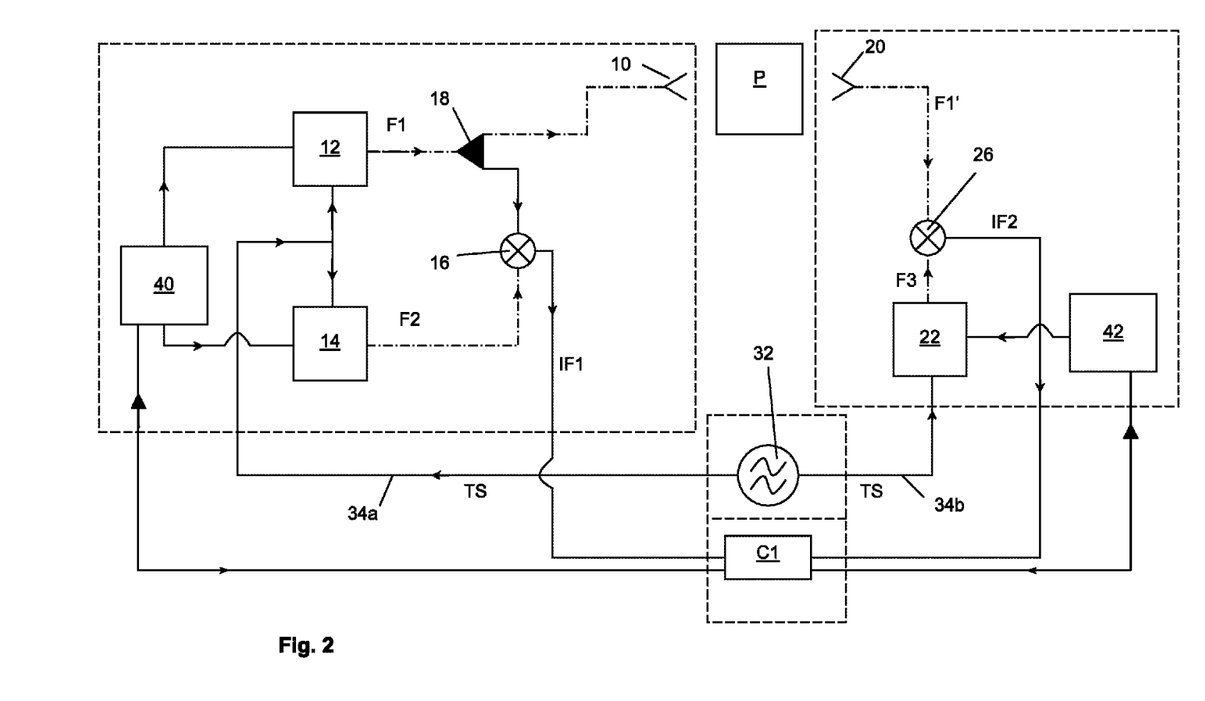
FIG. 2 A circuit diagram for a second exemplary embodiment of the invention, wherein the measuring principle used is the same as for the first exemplary embodiment.

With the above-described exemplary embodiment, the high-frequency signals generated by the synthesizers 12, 14, 22 cannot be changed. Oftentimes, however, a measuring with different high frequencies is desired, wherein it always applies that the second high frequency of the second transmitting-side synthesizer 14 and the third high frequency of the receiving-side synthesizer 22 are identical, and these two second and third high frequencies are slightly different from the first high frequency of the first transmitting-side synthesizer 12. In that case, it is necessary to ensure that the synthesizers 12, 14, 22 can be controlled by a controller. In principle, the central processor can take over this task, wherein it is preferable for long geometric distances if the controlling is not realized directly by the central processor, but occurs respectively via a transmitting-side controller 40 and a receiving-side controller 42 which, in turn, are controlled by the central processor 30 (FIG. 2).

Of course, since it is indispensable for the success of the invention that the synthesizers have a phasing, known to each other, their coupling to the frequency standard not only must be phase-locked, but also reproducible. It means that during the switch-on or for a change in the frequency, the same phase always adjusts for all synthesizers. However, a plurality of synthesizers known from the prior art exhibit this feature, so that no additional measures are required to achieve reproducibility.

Figure 4:
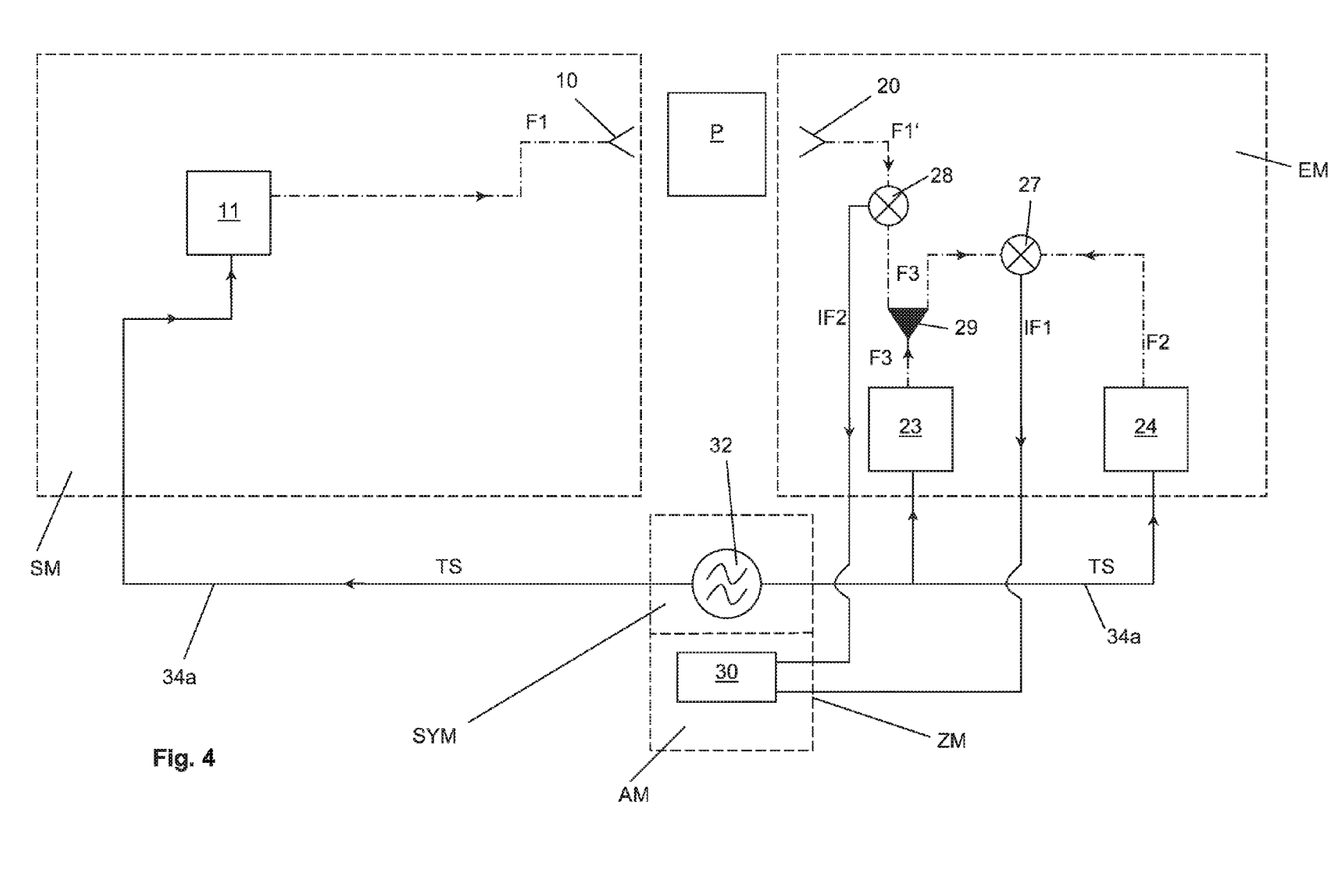
FIG. 4 An alternative circuit diagram.

With the aid of the synthesizers, coupled phase-locked reproducible, both intermediate frequencies IF1 and IF2 can also be generated on the receiver side, so that the connecting cable for this signal between the transmitting module SM and the evaluation module AE can be omitted. A concrete exemplary embodiment is shown in FIG. 4. In that case, the transmitting module SM is provided with only one synthesizer 11. All other components are integrated into the receiving module EM which thus has a first and a second synthesizer 23, 24, wherein the second synthesizer 24 generates a second high-frequency signal F2 that has the same high frequency as the first high-frequency signal F1 from the transmitting-side synthesizer 11 (for example again 3 GHz), while the first synthesizer 23 (as for the above-described example) generates a third high-frequency signal F3 with a slightly different high frequency (for example again 3.001 GHz). The first intermediate frequency signal IF1 is generated by mixing the second high-frequency signal F2 with the third high-frequency signal F3, using the first receiving-side mixer 27 of which one input is connected via a power divider 29 to the first receiving-side synthesizer 23. The second intermediate frequency signal IF2 is generated as described in the above by using the second receiving-side mixer 28 which corresponds to the receiving-side mixer 26 of the first exemplary embodiment. As for the above-described example, all synthesizers 11, 23, 24 are clocked phase-locked by the frequency standard 32.

Figure 5:
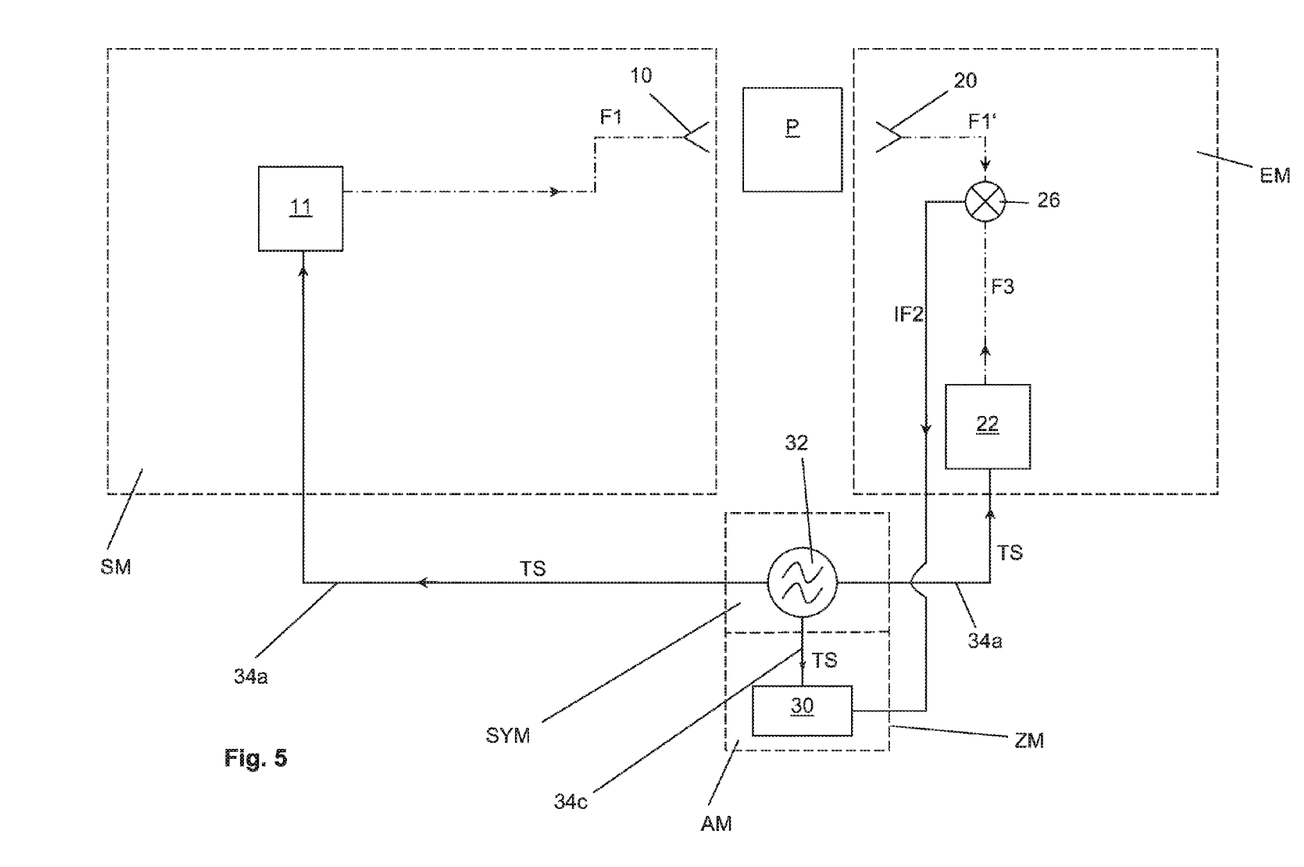
FIG. 5 A further alternative circuit diagram.

FIG. 5 shows a further embodiment, provided with only one transmitting-side frequency generator 11 for generating a first high-frequency signal F1 and only one receiving-side frequency generator 22 for generating an additional high-frequency signal, which is referred to as third high-frequency signal F3 for the sake of consistency. In this case, the clocking signal TS of the synchronization module functions directly as the reference signal (in the previous embodiments, it was the first intermediate frequency signal IF1) or, if applicable, a signal derived directly therefrom. If the clocking signal TS is to be used directly as the reference signal, as shown in the exemplary embodiment according to FIG. 5, for which an additional low-frequency synchronization signal line 34c is provided to connect the frequency standard 32 with the central processor, then the frequency of the second intermediate frequency signal IF2 (of the mixing signal from F3 and F1') must be the same as the frequency of the clocking signal TS. If the clocking signal TS frequency in this case is also 10 MHz, then the frequency of the first high-frequency signal F1 could be 3 GHz and the frequency of the third high-frequency signal F3 could be 3.01 GHz. This exemplary embodiment leads to a simplified circuit.

Figure 6:
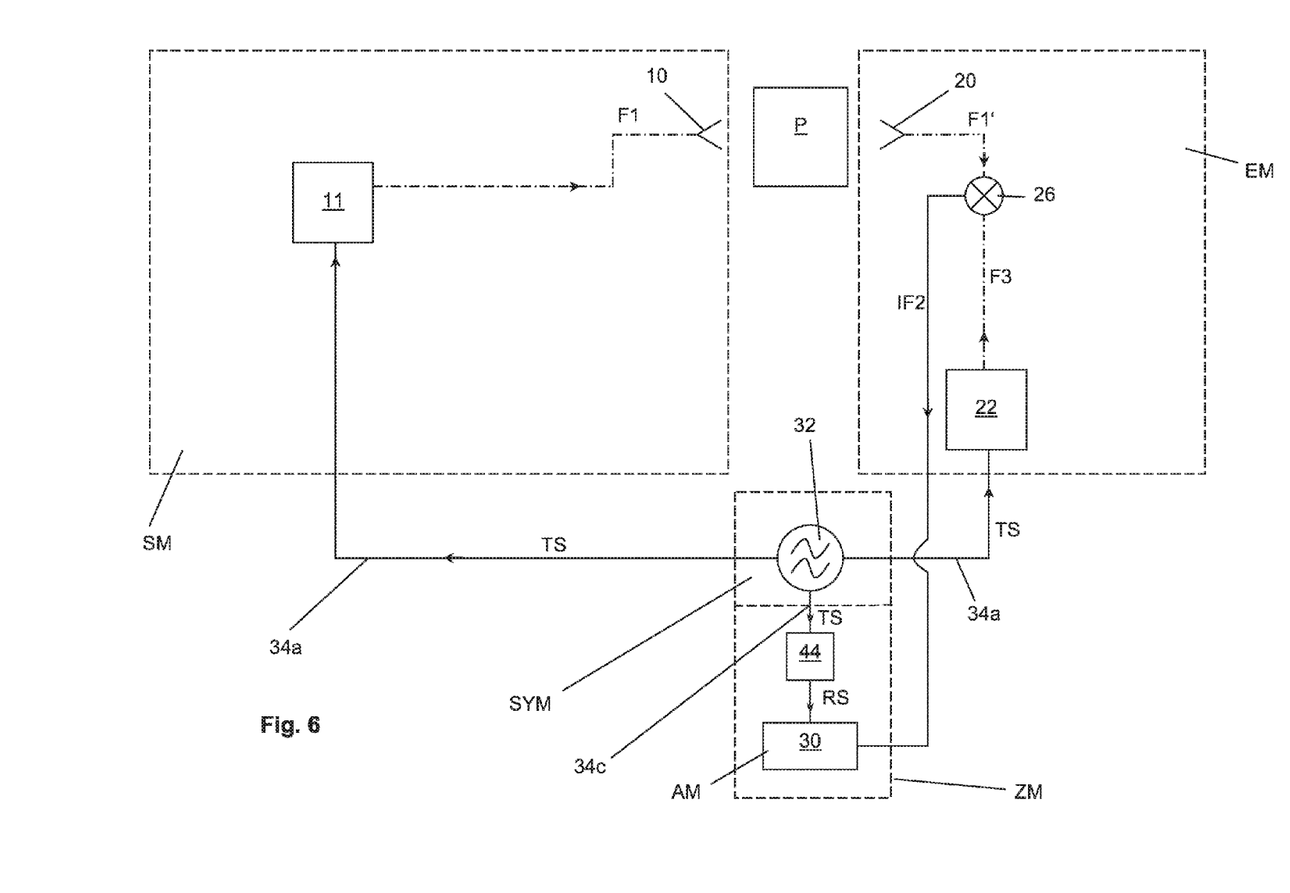
FIG. 6 A further alternative circuit diagram.

This course of action can be generalized: The frequency of the intermediate-frequency signal IF2 coming from the receiving module need not be identical to the frequency of the clocking signal TS of the frequency standard 32. It is only necessary that both signals are coupled phase-locked reproducible. As shown in FIG. 6, it is for example possible to provide a frequency converter, in particular a low-frequency synthesizer 44 which generates a reference signal RS, between the frequency standard 32 and the central processor 30 that functions as an evaluation unit. The frequency of this reference signal corresponds to the frequency of the second intermediate signal IF2, for example 1 MHz at f(F1)=3 GHz and f(F3)=3.001 GHz. The exemplary embodiment shown in FIG. 6 thus corresponds essentially to the embodiment in FIG. 4, with the difference that the first intermediate reference signal lF1, which is obtained by mixing the two high-frequency signals F2 and F3 and which functions as reference, is replaced by the non-mixed reference signal RS that is generated directly by the low-frequency synthesizer 44.

The invention has been described with the aid of a heterodyne system which is also the preferred embodiment. However, the invention can also be used with a homodyne system. In that case, only one transmission-side synthesizer and one receiving-side synthesizer are provided, which generate the same high frequency. The phase-locked coupling of these two synthesizers via a joint frequency standard is identical to the example shown in the above.

Figure 7:
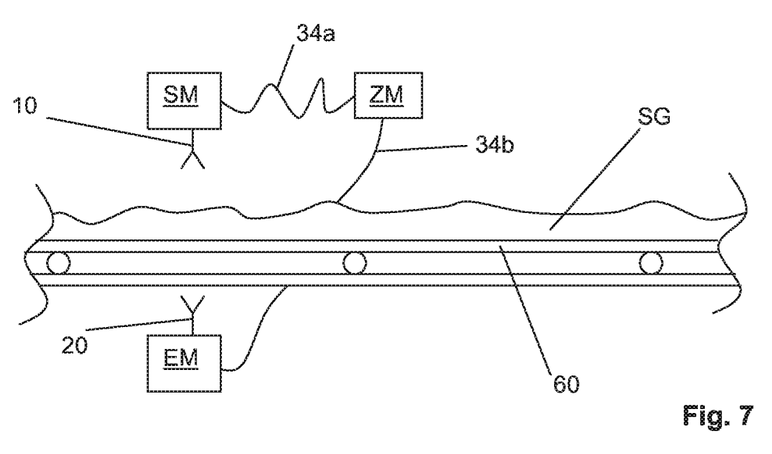
FIG. 7 A first preferred use of the invention.
Figure 8:
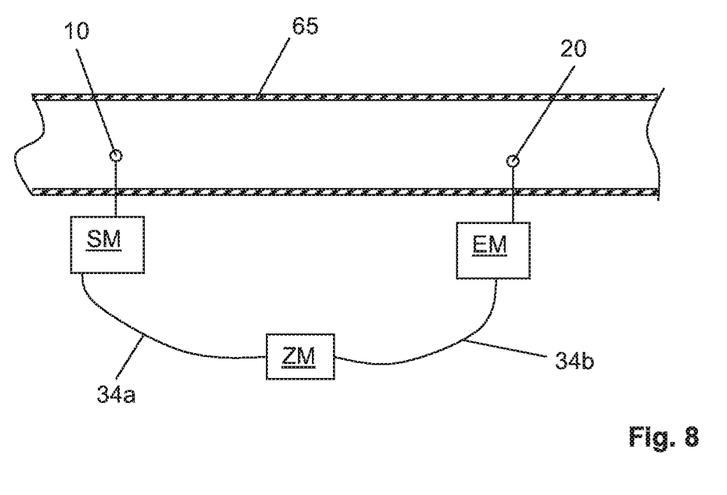
FIG. 8 A second preferred use of the invention.

As previously mentioned, the advantages of the improvement according to the invention are particularly obvious when the device is used on an industrial scale, for example for the online measuring of bulk goods SG such as coal or iron ore conveyed on a conveying belt 60 (FIG. 7), or for the online measuring of fluid streaming through a pipe (65) (FIG. 8), wherein the measuring inside a container is possible as well.

LIST OF REFERENCES 10 transmitting antenna
11 transmitting-side synthesizer
12 first transmitting-side synthesizer
14 second transmitting-side synthesizer
16 transmitting side mixer
18 power divider
18a first power divider
18b second power divider
20 receiving antenna
22 receiving-side synthesizer
23 first receiving-side synthesizer
24 second receiving-side synthesizer
26 receiving side mixer
27 first receiving side mixer
28 second receiving side mixer
29 power divider
30 central processor (evaluation unit)
32 frequency standard
34a transmitting-side low-frequency synchronization signal line
34b receiving-side low-frequency synchronization signal line
34c additional low-frequency synchronization signal line
40 transmitting-side controller
42 receiving-side controller
44 low-frequency synthesizer
50 high-frequency reference line
60 conveyor belt
65 pipe
F1 first high-frequency signal with first frequency
F2 second high-frequency signal with second frequency
F3 third high-frequency signal with third frequency
lF1 first intermediate-frequency signal with first intermediate frequency
lF2 second intermediate-frequency signal with second intermediate frequency
TS clocking signal
RF reference signal
SM transmitting module
EM receiving module
AE evaluation unit
SYM synchronization module
ZM central module
SG bulk goods

The invention claimed is:

1. A device for measuring at least one of dielectric and magnetic properties of a sample by means of a microwave transmission measurement, said device comprising:
 a transmitting antenna and a receiving antenna defining a transmission measuring section in which the sample to be measured is located;
 a transmitting module comprising a first transmission-side synthesizer and a second transmission-side synthesizer for generating high-frequency signals with a frequency between 800 MHz and 30 GHz;
 a clock, connected via a transmitting-side low-frequency synchronization signal line to the first and second transmission-side synthesizers, the first and second transmission-side synthesizers being coupled to the clock to be phase-locked reproducible;
 a transmitting side mixer configured to generate an intermediate-frequency signal based on the high-frequency signals from the first and second transmission-side synthesizers;
 an evaluation unit configured to receive the intermediate-frequency signal from the transmitting-side mixer; and
 a receiving module which is spatially remote from the transmitting module, said receiving module comprising a receiving-side synthesizer and a receiving side mixer, wherein the receiving-side synthesizer is connected to the clock by means of a receiving-side low-frequency synchronization signal line and is coupled to be phase-locked reproducible,
 wherein the transmission antenna is configured to receive the high frequency signal from the first transmission-side synthesizer,
 the receiving-side mixer is configured to receive the high-frequency signal from the receiving antenna and a second high-frequency signal generated by the receiving-side synthesizer, to generate a second intermediate-frequency signal based on the high-frequency signal from the receiving antenna and the second high-frequency signal, and to supply the second intermediate-frequency signal to the evaluation unit, and
 the second transmission-side synthesizer and the receiving-side synthesizer are configured to generate high-frequency signals having the same frequency, and the first transmission-side synthesizer is configured to generate a high-frequency signal different from the second transmission-side synthesizer.

2. The device according to claim 1, further comprising:
 a frequency converter connected to the evaluation unit, the frequency converter configured to generate a reference signal having a frequency representing a difference between the high-frequency signal output from the first transmission-side synthesizer and the high-frequency signal output from the second transmission-side synthesizer.

3. The device according to claim 2, wherein the transmission measuring section intersects a conveyor belt.

4. The device according to claim 2, wherein the transmission measuring section is located inside a container.

5. The device according to claim 2, wherein the transmission measuring section is located inside a pipe.

6. A device for measuring one or both of dielectric and magnetic properties of a sample by means of a microwave transmission measurement, said device comprising:

a transmitting antenna and a receiving antenna which define a transmission measuring section in which the sample to be measured is located;

a transmitting module comprising one transmission-side synthesizer for generating a first high-frequency signal with a frequency between 800 MHz and 30 GHz;

a clock, connected via a transmitting-side low-frequency synchronization signal line to the transmitting side synthesizer, the clock being coupled to the transmitting-side synthesizer to be phase-locked reproducible;

an evaluation unit; and a receiving module which is spatially remote from the transmitting module, said receiving module comprising:

a first receiving-side synthesizer configured to generate a second high-frequency signal;

a second receiving-side synthesizer configured to generate a third high-frequency signal;

a first receiving side mixer configured to receive the second and third high-frequency signals from the first and second receiving-side synthesizers, to generate an intermediate-frequency signal based on the second and third high-frequency signals, and to supply the intermediate-frequency signal to the evaluation unit, wherein the first and second receiving-side synthesizers are connected to the clock by means of a receiving-side low-frequency synchronization signal line and are coupled to the clock to be phase-locked reproducible, the first high-frequency signal from the transmitting-side synthesizer is supplied to the transmitting antenna, the receiving antenna is configured to receive the first high-frequency signal from the transmitting antenna, the second receiving-side mixer is configured to receive the first high-frequency signal from the receiving antenna and the second high-frequency signal from the first receiving-side synthesizer, and to generate a second intermediate-frequency signal based on the first and second high-frequency signals, and the transmitting-side synthesizer and the second receiving-side synthesizer are configured to generate the first high-frequency signal and the third high-frequency signal, respectively, to have a same frequency, and the first receiving-side synthesizer is configured to generate the second high-frequency signal to have a frequency different from the first and third high-frequency signals.

* * * * *